United States Patent
Pohlmann et al.

(10) Patent No.: US 10,266,480 B2
(45) Date of Patent: Apr. 23, 2019

(54) METHOD AND DEVICE FOR REMOVING CONTAMINANTS ARISING DURING THE PRODUCTION OF ALIPHATIC NITRATE ESTERS

(71) Applicant: Josef Meissner GmbH & Co. KG, Cologne (DE)

(72) Inventors: Jurgen Pohlmann, Cologne (DE); Heinrich Hermann, Cologne (DE); Mirko Handel, Neunkirchen-Seelscheid (DE); Jurgen Gebauer, Troisdorf (DE)

(73) Assignee: Josef Meissner GmbH & Co. KG, Köln (DE)

( * ) Notice: Subject to any disclaimer, the term of this patent is extended or adjusted under 35 U.S.C. 154(b) by 0 days.

(21) Appl. No.: 14/912,387

(22) PCT Filed: Jun. 25, 2014

(86) PCT No.: PCT/EP2014/063334
§ 371 (c)(1),
(2) Date: Feb. 16, 2016

(87) PCT Pub. No.: WO2015/022110
PCT Pub. Date: Feb. 19, 2015

(65) Prior Publication Data
US 2016/0200663 A1    Jul. 14, 2016

(30) Foreign Application Priority Data

Aug. 15, 2013  (DE) .......... 10 2013 013 474
Oct. 2, 2013   (DE) .......... 10 2013 110 952

(51) Int. Cl.
*B01J 19/00*    (2006.01)
*B01J 19/18*    (2006.01)
(Continued)

(52) U.S. Cl.
CPC ........ *C07C 201/02* (2013.01); *B01D 11/0473* (2013.01); *B01J 19/1812* (2013.01); *C07C 203/04* (2013.01)

(58) Field of Classification Search
CPC ........ B01J 19/00; B01J 19/18; B01J 19/1812; B01J 19/24; B01J 19/2415; B01J 19/32;
(Continued)

(56) References Cited

U.S. PATENT DOCUMENTS 2,977,384 A * 3/1961 Bentley ............... C07C 201/02
                                                     558/480
6,670,506 B2 * 12/2003 Knott ................. C07C 241/00
                                                     564/109
9,115,048 B2 * 8/2015 Pohlmann ........... C07C 201/16

FOREIGN PATENT DOCUMENTS

WO    WO 2012/156095 A1 * 11/2012

* cited by examiner

*Primary Examiner* — Natasha E Young
(74) *Attorney, Agent, or Firm* — Edward E. Sowers; Brannon Sowers & Cracraft PC (57) ABSTRACT

The invention relates to a method and to a device for removing contaminants arising during the production of aliphatic or alicyclic nitric acid esters, in particular for removing contaminants from nitrated crude nitric acid esters, which nitrated crude nitric acid esters arise during the nitration of monovalent or multivalent aliphatic or alicyclic alcohols capable of nitration, after the separation of the final nitrating acid, and to a production system for nitrating monovalent or multivalent aliphatic alcohols capable of nitration with subsequent purification of the nitrated nitric acid esters.

16 Claims, 4 Drawing Sheets

(51) Int. Cl.
  *B01D 11/04* (2006.01)
  *C07C 201/02* (2006.01)
  *C07C 203/04* (2006.01)
(58) Field of Classification Search
  CPC ..... B01D 11/00; B01D 11/04; B01D 11/0446;
         B01D 11/0473; C07C 201/00–201/02;
                                C07C 203/00–203/04
  See application file for complete search history.

METHOD AND DEVICE FOR REMOVING CONTAMINANTS ARISING DURING THE PRODUCTION OF ALIPHATIC NITRATE ESTERS

CROSS-REFERENCES TO RELATED APPLICATIONS

This application is a National Stage filing of International Application PCT/EP 2014/063334, now WO 2015/022110, filed Jun. 25, 2014, claiming priority to DE 10 2013 013 474.9 filed Aug. 15, 2013, and to DE 10 2013 110 952.7 filed Oct. 2, 2013, entitled "METHOD AND DEVICE FOR REMOVING CONTAMINANTS ARISING DURING THE PRODUCTION OF ALIPHATIC NITRATE ESTERS". The subject application claims priority to PCT/EP 2014/063334, now WO 2015/022110, DE 10 2013 013 474.9 and DE 10 2013 110 952.7 and incorporates all by reference herein, in their entirety.

BACKGROUND OF THE INVENTION

The present invention relates to the technical field of the preparation of nitric esters (also referred to synonymously as nitroesters or nitrate esters) of monohydric or polyhydric (cyclo)aliphatic alcohols (i.e. in other words, the nitration of monohydric or polyhydric aliphatic or cycloaliphatic alcohols to form the corresponding nitric esters), in particular the purification of the crude nitrated nitric esters obtained after removal of the residual nitrating acid.

The present invention relates in particular to a process for removing impurities (in particular unreacted starting materials, reaction by-products, nitrating acid and reaction products thereof, e.g. nitrogen oxides or nitrous acid, etc.) obtained in the preparation of aliphatic or cycloaliphatic nitric esters, in particular a process for removing impurities from crude nitrated nitric esters obtained in the nitration of nitratable monohydric or polyhydric aliphatic or cycloaliphatic alcohols after removal of the residual nitrating acid.

Furthermore, the present invention relates to an apparatus or plant for removing impurities obtained in the preparation of aliphatic or cycloaliphatic nitric esters, in particular an apparatus or plant for removing impurities from crude nitrated nitric esters obtained in the nitration of nitratable monohydric or polyhydric aliphatic or cycloaliphatic alcohols after removal of the residual nitrating acid.

Finally, the present invention relates to a production plant for the nitration of nitratable aliphatic or cycloaliphatic alcohols with subsequent purification of the crude nitrated products (i.e. with subsequent purification of the resulting crude nitric esters) or a production plant for the preparation of nitric esters of monohydric or polyhydric aliphatic or cycloaliphatic alcohols with subsequent purification of the crude nitrated products.

Aliphatic nitroesters (also referred to synonymously as aliphatic nitric esters, aliphatic nitrate esters or the like), e.g. pentaerythrityl tetranitrate (PETN), glyceryl trinitrate (NGL), ethylene glycol dinitrate (EGDN), ethylhexyl nitrate (EHN), etc., are generally prepared in a continuously operated plant (e.g. in the case of NGL, EGDN or mixtures thereof by the process of Schmid-Meissner or Biazzi, by the injector process or by the N.A.B. process of Nielsen and Brunnberg or in the case of EHN by a modified process as described in EP 1 792 891 A1) by reaction of the corresponding alcohol (e.g. pentaerythritol, glycerol, ethylene glycol, ethylhexylethanol, etc.) with nitric acid either directly and alone or else in the presence of sulfuric acid as catalyst and water-binding agent. The nitration of the alcohols (i.e. the reaction thereof to form nitric esters) is generally carried out in the liquid phase, either as pure substance or else as a mixture or else in solution in inert, water-immiscible solvents.

The resulting crude nitroesters (hereinafter also referred to synonymously as crude nitric esters, crude nitrate esters, crude nitrated products or the like) have to be subjected before further processing thereof to multistage washing and additional purification steps in order to remove impurities which are still dissolved or suspended in the crude nitroesters, e.g. sulfuric acid, nitric acid, nitrous gases, etc., and by-products from the oxidative degradation of the starting alcohols, and thus improve the stability of the nitroesters, which are largely highly sensitive explosive materials.

The washing of the crude nitroesters in order to remove the dissolved and suspended acids of the nitration mixture and other acidic impurities or impurities which can be extracted in another way by the washing medium usually consists of three steps (see, for example, T. Urbanski, Vol. 2, pages 97 ff., in particular FIGS. 43, 44, 59 and 60, Pergamon Press, Reprint 1985). Water is usually employed as washing medium for this purpose. Washing is generally carried out as a liquid/liquid wash using the nitroester which is liquid at the washing temperature or as a solution of the nitroester in a suitable solvent.

This three-stage wash of the crude nitrated products (i.e. the crude nitroesters or nitric esters) usually comprises the following steps:
1. an acid wash ("acid wash") with water to remove the dissolved and suspended mineral acids, e.g. sulfuric acid, nitric acid and nitrous gases;
2. a basic or alkali wash ("basic wash" or "alkali wash") in the presence of a base, e.g. sodium carbonate (soda), sodium bicarbonate, ammonia, sodium hydroxide, potassium hydroxide, etc., in particular for removing the mineral acids still present in the nitrate ester after the first wash and residues of nitrous gases and other weakly acidic impurities from oxidative decomposition of the alcohol used or other aliphatic or cyclic hydrocarbons which were present as traces in the starting alcohol;
3. a wash with water ("neutral wash") for removing the residual traces of alkali and for further in traces in the product.

However, washing of the crude nitrate esters directly with soda solution, i.e. with omission of the "acid wash" stage, is sometimes also practiced and is prior art (see, for example, T. Urbanski, Vol. 2, Biazzi process, pages 107 ff., in particular FIG. 48, Pergamon Press, Reprint 1985; T. Urbanski, Vol. 4, page 328, Pergamon Press 1984; B. Brunnberg, Industrial and Laboratory Nitration, ACS Symposium Series No. 22 (Editors: L. F. Albright and H. J. T. Hanson), page 341, Washington D.C., 1976).

The objective of these washing steps is to obtain not only a pure product having high stability but also very little wastewater per metric ton of product; the washed-out impurities and the nitrate ester (traces) still present as a function of their solubility should be present in the wastewater in such amounts that they can be disposed of inexpensively.

To minimize the amount of water required for this wash and to recover the acids dissolved in the crude nitrate esters in appreciable amounts, specially nitric acid, the wash can, as described, for example, in DE-C 505 424 and DE-C 546 718, be carried out using a reduced amount of washing water in the first washing step ("acid wash") in such a way that a washing acid having a content of nitric acid of from 20 to 60% strength or of from 35 to 55% and a content of sulfuric acid of up to 15% is obtained. This washing acid can be worked up directly or together with the residual nitrating acid.

Furthermore, washing can, for example, be carried out in countercurrent by feeding the washing water from the third washing step ("neutral wash") either directly or after addition of bases to the washing of the nitrate ester in the second washing step ("alkali wash") and introducing this washing water from the second washing step (i.e. the alkaline washing stage) into the first washing step (i.e. the acid wash) (cf. DE-C 505 424 and DE-B 1 135 876).

It is usual, for reasons of safety, to give preference to using injectors (jet pumps) as conveyors using the washing medium as driving medium between the individual washing steps in these three washing steps and carrying out the actual wash in air-operated washing columns. After washing is complete, the purified nitrate ester is transported as emulsion with water into a storage facility or to further processing.

DE-C 710 826 describes a process in which the three-stage washing of nitrate esters of polyhydric alcohols is carried out in countercurrent in washing columns stirred by means of air, with the nitrate esters being premixed with the washing liquid in injectors and this premixed emulsion being fed by means of air injectors into the washing column. At the end of the wash, the washed nitrate ester is, after phase separation by means of injectors which are operated using circulated driving water, transported to the storage facility. In the washing processes documented in T. Urbanski, Vol. 2, pages 97 ff., in particular FIGS. 59 and 60, Pergamon Press, Reprint 1985, too, the washing process described in DE-C 710 826 is used in combination with the injector process.

To remove a material from a mixture of materials by extraction/washing in a material which is immiscible with this mixture of materials, as in the present case of the mixture of liquid nitrate esters/impurities with water, it is necessary, in order to achieve successful extraction of the impurities from the mixture of materials, to disperse the two immiscible phases in one another, whether as oil-in-water emulsion (O/W emulsion) or as water-in-oil emulsion (W/O emulsion), in such a way that there is a sufficiently large exchange area between the immiscible phases over a sufficiently long time for the partition equilibrium for the materials to be extracted to be reached and the extracted material in the extract phase to be able to be altered by means of subsequent reactions in such a way that backextraction is no longer possible.

It is known that injectors or jet pumps are suitable for mixing miscible liquids but that injectors are unsuitable as dispersing device for dispersing two immiscible liquids in one another. The droplet sizes generated in the injector are not small enough for good washing. The stability of the emulsion produced is too low and the exchange area required for optimal mass transfer is, in combination with the short residence time in the mixture tube of the injector (about 1 second), therefore too small.

The relatively unstable nitrate ester emulsions in water which are produced using injectors therefore tend to undergo quick phase separation. This is particularly problematical for transport of such emulsions over relatively long distances. As DE-C 973 718 appears to describe, if an emulsion is conveyed alone, separation into explosive oil and water easily takes place in the long transport pipes having a small inclination. It is possible for a contiguous explosive oil layer to be formed, and this makes detonation throughout possible.

To prevent coalescence of the nitrate esters after leaving the injector and especially to prevent detonation throughout of explosive oil which has separated out during transport of the emulsion, methods which allow the emulsion of the nitrate ester in water to be stabilized and the formation of liquid threads of nitrate esters which have separated out, which are capable of detonation throughout, to be prevented have been reported, for example as described in U.S. Pat. No. 2,140,897 A, DE-C 820 575, DE-C 973 718, DE-B 1 058 093, DE-A 1 571 221 or DE-A 2 055 093. This is preferably brought about by mixing in of air or by re-emulsification using air or else by interrupting the emulsion stream with water or air.

However, it is known that gas bubbles in the liquid nitrate ester can not only significantly increase its shock sensitivity, caused by adiabatic compression (cf. DE-A 1 571 221), but that the two-phase mixtures comprising additionally drawn-in air, as previously described in DE-B 1 058 039, can lead to such stable emulsions that phase separation is possible only by use of centrifugal separators.

This risk of air inclusion in the liquid nitrate ester can be prevented by the measures described in DE-A 1 571 221 and DE-A 2 055 093. Interruption of the homogeneous emulsion column in the transport conduit by a nitrate ester-free water column effectively prevents formation of an explosive thread capable of detonation throughout by rapid coalescence of the nitrate ester emulsified in the injector.

The relatively unstable dispersions of nitrate ester in washing water or vice-versa which are produced by the injector with its relatively low dispersing power and the resulting nonoptimal exchange area for effective washing (additionally in combination with the very short residence times in the mixing region of the injector) allow only incomplete removal of the impurities in the nitrate ester to be purified. In order to achieve the desired purities, the injectors are therefore coupled with residence vessels with active dispersing.

For this reason, air-operated washing columns (DE-C 710 826) in combination with injectors as transport means or cascades of stirred vessels in combination with injectors (T. Urbanski, Vol. 4, page 328, in particular FIG. 46, Pergamon Press 1984) are usually used as washing apparatuses for washing the nitroesters to be purified in the individual washing stages. The use of the air-stirred washing columns is complicated and expensive and is no longer in accordance with present-day safety standards according to which the presence of air bubbles in the nitrate ester should be avoided (DE-A 1 571 221). Multistage cascades of stirred vessels are also complicated and expensive.

The use of injectors alone, i.e. without residence vessel, as proposed in DE-B 1 039 049 is also complicated and expensive. In order to achieve optimal purification by means of injectors without residence vessel and additional dispersing devices, each washing step has to be carried out in a plurality of stages in order to be able to obtain the desired purity and stability for further processing of the nitrate ester.

The emulsion transport of nitrate esters, as described in DE-A 1 571 221 and in DE-A 2 055 093, is relatively unsuitable as additional washing stage because it has only at most a polishing effect in order to remove traces of washing medium which have been carried as microemulsion from the preceding washing stages because of its relatively unstable emulsion with relatively large droplets produced by an injector.

Overall, the processes and plants for purifying nitrate esters which are known from the prior art either do not operate with high efficiency or else they are no longer satisfactory from the point of view of modern safety standards.

BRIEF SUMMARY OF THE INVENTION

It is therefore an object of the present invention to provide a process and an apparatus for removing impurities obtained in the preparation of aliphatic nitrate esters, in particular for removing impurities from crude nitrated nitrate esters obtained in the nitration of nitratable monohydric or polyhydric aliphatic alcohols after removal of the residual nitrating acid, and also a (production) plant for the nitration of nitratable monohydric or polyhydric aliphatic alcohols with subsequent purification of the nitrated nitric esters, with the abovementioned problems and disadvantages occurring in connection with the prior art being at least largely avoided.

In particular, it is an object of the present invention to provide a process and an apparatus or plant suitable for carrying out this process, by means of which efficient purification of the nitrate esters as are obtained from the nitration of monohydric or polyhydric alcohols after removal of the residual nitrating acids can be made possible.

A further object of the present invention is to carry out the washing of the crude nitrate esters which result after removal of the residual nitrating acid or solutions thereof in inert solvents, in which significant amounts of impurities, for example entrained nitrating acid, dissolved sulfuric acid, nitric acid, nitrous gases, degradation products from the oxidative degradation of the starting alcohols, etc., can be present, in one stage in each washing step in such a way that the washed nitrate esters are free of acids and water-soluble and acidic residues from the oxidative degradation of the starting alcohol to be nitrated and/or of the product, so that the product which has been treated in this way meets the respective requirements in terms of its stability, other safety-related requirements and further product specifications and safety in the plant thus increases as a result of a further reduction in the amounts of nitrate esters in the plant and, finally, the complication and costs associated therewith are thus considerably lower than in the previously utilized processes and apparatuses of the prior art.

The objects indicated above are achieved according to the invention by a process as claimed herein; further, advantageous further developments and embodiments of the process of the invention are subject matter of the dependent claims relating thereto.

The present invention further provides an apparatus or a plant as claimed in the relevant independent claim (secondary claim); further advantageous developments and embodiments of this aspect of the invention are subject matter of the dependent claims relating thereto.

In addition, the present invention provides a production plant as claimed in the relevant independent claim (secondary claim); further advantageous developments and embodiments of this aspect of the invention are subject matter of the dependent claims relating thereto.

It goes without saying that embodiments, variants, advantages or the like which are indicated below for only one aspect of the invention in order to avoid unnecessary repetition also apply analogously to the other aspects of the invention.

Furthermore, it goes without saying that when values, numbers and ranges are given, the respective values, numbers and ranges indicated do not constitute a restriction; in addition, it will be obvious to a person skilled in the art that, depending on an individual case or depending on the use, the ranges or figures indicated can be deviated from without going outside the scope of the present invention.

In addition, all values and parameters or the like indicated below can in principle be measured or determined using standardized or explicitly indicated methods of determination or else by the methods of determination with which a person skilled in this field will be familiar per se.

This having been said, the present invention will be described in more detail below.

DETAILED DESCRIPTION OF THE INVENTION

The present invention therefore provides, according to a first aspect of the present invention, a process for removing impurities obtained in the preparation of aliphatic or cycloaliphatic nitric esters (nitrate esters or nitroesters), in particular a process for removing impurities from crude nitric esters obtained in the nitration of nitratable monohydric or polyhydric aliphatic or cycloaliphatic alcohols after removal of the residual nitrating acid, by treatment with at least one washing medium, wherein the process comprises the following process steps:

(a) the crude nitric esters (i.e. the crude nitrated products obtained after removal of the residual nitrating acid) are firstly brought into contact with a washing medium, with the crude nitric esters and the washing medium being dispersed in one another in such a way that an emulsion results (i.e. in other words, an emulsion or dispersion of firstly crude nitrated products and secondly washing medium is produced in this first process step (a)); and (b) the resulting emulsion is subsequently fed into a tube reactor which is equipped with mixing elements, in particular for introducing additional mixing energy, so that the impurities initially present in the crude nitric esters are at least partly removed during passage of the emulsion through the tube reactor and/or so that the impurities initially present in the crude nitric esters are at least partly transferred into the washing medium and/or neutralized thereby during passage of the emulsion through the tube reactor.

The process of the invention is thus outstandingly suitable for purifying crude nitrated products obtained in the nitration of nitratable monohydric or polyhydric aliphatic alcohols after removal of the residual nitrating acid (i.e. in other words, for purifying the resulting crude nitric esters).

The principle of the process of the invention is, inter alia, that the crude nitrate esters which come from the nitration and still contain significant amounts of impurities are, after removal of the residual nitrating acid (e.g. in a separator), are firstly brought into contact with a washing medium and the mixture of nitrate ester to be purified and washing medium is converted into an emulsion or dispersion and the resulting emulsion or dispersion is subsequently fed into a tube reactor so that the impurities initially present in the nitrate esters to be purified are transferred into the washing medium or neutralized thereby and a purified nitrate ester is formed in this way.

Typical impurities to be removed encompass, for example, unreacted starting materials (i.e. in particular, unreacted monohydric or polyhydric aliphatic or cycloaliphatic starting alcohols and unreacted starting mineral acids, especially nitric acid and possibly sulfuric acid, if used as starting material) and reaction by-products (in particular reaction products of nitric acid, e.g. nitrous acid, nitrous gases, etc., and reaction by-products of the starting alcohols, e.g. oxidation products such as carboxylic acids, aldehydes, ketones, degradation or dissociation products, carbon dioxide, etc.).

As the applicant has discovered in a completely surprising way, the use of a tube reactor with additional mixing elements, in combination with an upstream dispersing or emulsifying device, leads to particularly good mixing and particularly intimate and fine dispersion of firstly washing medium and secondly nitrate esters to be purified or solutions thereof being able to be achieved, so that the impurities can be removed completely or at least essentially completely in this way in a single process step (namely during the treatment in the tube reactor).

In contrast to the prior art, further complex process steps for purifying the crude nitroester are thus avoided in an efficient way without impairment of quality having to be accepted in the purification of the crude nitrate ester. The required safety standards are also ensured by the process of the invention.

The tube reactor with additional mixing elements used with the washing medium according to the invention for the treatment of the crude nitrate ester surprisingly ensures, in combination with the upstream dispersing device for producing the starting emulsion of washing medium and crude nitroester, such intimate and fine dispersion of firstly crude nitroester and secondly washing medium that all or at least essentially all impurities are transferred into the washing medium or neutralized thereby during the tube reactor treatment as per process step (b), so that they can subsequently (i.e. after conclusion of process step (b)) be separated off together with the washing medium from the then purified nitrate ester.

It has surprisingly been found that it is possible within the framework of the present invention to successfully carry out washing of nitrate esters in virtually one stage, even at a high loading with impurities such as nitrating acid, nitric acid, etc., and by means of a simple and inexpensive combination of jet pumps (injectors) or jet mixers (jet mixing devices), or else other dispersing devices, in combination with additional devices such as static mixers, orifice plates, etc., in the downstream tube reactor, which makes it possible not only to introduce a precisely defined quantity of mixing energy into the mixture of the immiscible phases but also ensure a residence time which allows even subsequent reactions to proceed virtually quantitatively. The emulsions of the organic phase to be purified in the washing medium (O/W type) or of the washing medium in the organic phase (W/O type) which can be produced thereby provide the interfacial area between the nitrate ester to be washed and washing medium which is required for effective and optimal mass transfer.

A further special feature of the present invention is that the tube reactor is equipped with mixing elements, in particular static mixing elements, for introducing additional mixing energy (where the mixing elements can, for example, be configured as plates, in particular impingement or deflection plates, as orifice plates, as static mixers or as flow dividers). This leads to the original droplet size distribution not only being maintained but also being set in such a way that the impurities initially present in the crude nitrated products are completely transferred into the washing medium and/or neutralized thereby during passage of the emulsion through the tube reactor.

As regards the aliphatic nitric ester (nitrate ester) to be purified, this can be selected from among any nitric esters of monohydric or polyhydric aliphatic alcohols. In particular, the nitric ester to be purified can be selected from among (i) nitric esters of aliphatic or cycloaliphatic monoalcohols, in particular of linear or branched aliphatic or cycloaliphatic monoalcohols, in particular of hexanols, heptanols, octanols, ethylhexyl alcohol and cyclohexanol; (ii) nitric esters of dihydric aliphatic alcohols, in particular of ethylene glycol and propylene glycol and oligomers and polymers thereof, e.g. ethylene diglycol or propylene diglycol, ethylene triglycol or propylene triglycol and polyethylene glycol or polypropylene glycol; (iii) nitric esters of trihydric aliphatic alcohols, in particular of trimethylolethane and glycerol; (iv) nitric esters of tetrahydric or polyhydric aliphatic alcohols, in particular of pentaerythritol and dipentaerythritol.

As indicated above, the tube reactor used in process step (b) is equipped with mixing elements for introducing additional mixing energy. In this way, the original droplet size distribution can not only be maintained but can be set in such a way that the impurities initially present in the crude nitrated products are transferred into the washing medium or neutralized thereby during passage of the emulsion through the tube reactor.

In particular, the mixing elements present in the tube reactor are static elements, i.e., in particular, the mixing elements are configured as static mixing elements.

In a particular embodiment, the mixing elements, in particular the static mixing elements, can be fixed to the inside of the tube reactor, in particular be joined to the interior walls of the tube reactor, preferably permanently or else releasably.

In a further particular, alternative embodiment, the mixing elements can be configured as push-in elements. Here, the push-in elements can, if necessary as a function of the number and/or position, be inserted into the tube reactor or be positioned in the tube reactor.

In particular, the mixing elements can be configured as plates, in particular impingement or deflection plates, as orifice plates, as static mixers or as flow dividers.

In a further embodiment, from 1 to 15 mixing elements, in particular from 2 to 15 mixing elements, preferably from 2 to 10 mixing elements, particularly preferably from 2 to 5 mixing elements, are arranged in the tube reactor. This leads to particularly good emulsification of crude products to be purified and washing medium.

In this context, it is also advantageous for sufficient mixing energy for mixing crude products and washing medium to be provided by the mixing elements in the tube reactor. In this context, it is particularly advantageous for a total mixing energy (i.e. volume-based mixing energy) of from 20 to 1000 joule/liter, preferably from 25 to 500 joule/liter, particularly preferably from 30 to 200 joule/liter, to be introduced in the tube reactor.

In this context, the pressure drop per mixing element should be from 0.2 bar to 3.0 bar, preferably from 0.3 to 1.5 bar, particularly preferably from 0.3 to 0.8 bar.

Particularly suitable mixing elements are static mixing elements, especially in the form of static mixers. These are devices for the mixing of fluids, in which the flow motion alone brings about mixing and which do not have moving elements. They consist of flow-influencing elements in a tube; these alternately divide the stream of material and then combine it again, as a result of which mixing is achieved.

According to the invention, it is thus provided for the tube reactor for carrying out process step (b) to be equipped with mixing elements, in particular for introducing additional mixing energy, in order to prevent coalescence of the washing emulsion after a short time and thus incomplete extraction of the impurities to be removed from the nitrate ester to be purified; in this way, particularly good purification results can be obtained since further improved, particularly intimate dispersion of firstly washing medium and secondly nitrate ester to be purified can be achieved and maintained over the entire length of the tube reactor by means of the additional mixing elements. The additional mixing elements, preferably distributed over the tube reactor, can be, in particular, metal plates, in particular impingement or deflection plates, orifice plates, static mixers, flow dividers or the like, in order to maintain the emulsion of the O/W or W/O type. According to the invention, preference is given to from 1 to 15 mixing elements, in particular from 2 to 15 mixing elements, preferably from 2 to 10 mixing elements, particularly preferably from 2 to 5 mixing elements, being present in the tube reactor; these mixing elements can be distributed over the entire length of the tube reactor.

The mixing elements can preferably be inserted according to requirements as push-in elements into the tube reactor.

As regards the production of the emulsion or dispersion in process step (a), this is generally effected by means of a suitable dispersing or emulsifying device, in particular by means of a suitable mixing device.

For the purposes of the present invention, it is possible to use, for example, a jet mixer or a pump, in particular a jet pump (injector), as dispersing or emulsifying device, in particular as mixing device.

A jet pump (injector) is a pump in which the pumping action is produced by a liquid jet ("driving medium") which draws in, accelerates and compresses/transports another medium ("suction medium") by momentum exchange, as long as it is under sufficient pressure. The term injector usually refers to a jet pump which generates a superatmospheric pressure which thus has a predominantly compressing action.

For the purposes of the present invention, the dispersing or emulsifying device, in particular the mixing device, can produce, in particular, a driving jet (central jet) and an annular jet surrounding the driving jet. Here, preference is given to the driving jet being formed by the washing medium and the annular jet being formed by the crude nitric ester to be purified.

In a particular embodiment, a jet mixer or a jet pump (injector) is used as dispersing or emulsifying device, in particular as mixing device. In particular, the jet mixer or the jet pump can produce a preferably central driving jet and a medium surrounding the driving jet, in particular in the form of an annular jet, with the driving jet preferably being formed by the washing medium and the annular jet preferably being formed by the crude nitric esters to be purified (with the converse mode of operation also being possible in principle, i.e. the crude nitric ester to be purified as driving jet and washing medium as annular jet, although this embodiment is less preferred).

As jet mixers or jet pumps, it is in principle possible to use all types of jet mixers or jet pumps which allow the nitrate ester to be washed or the washing medium to be injected with high relative velocity by means of the central driving jet as free jet, which can in principle consist of either the washing medium or the nitrate ester to be washed, in such a way that either the nitrate ester to be washed is dispersed in the washing medium or the washing medium is dispersed in the nitrate ester to be washed as emulsion with high interfacial area. Apparatuses of this type are described, for example, in Ullmann's Encyclopedia of Industrial Chemistry, 2003, 5th Ed., Vol. B4, pages 87/88 and 565 to 571, or else in Perry's Chemical Engineers' Handbook, McGraw-Hill Book Company, 1984, 6th edition, pages 5-21 to 5-23, or else in the German patent document DE-A 2 151 206.

As indicated above, the (central) driving jet in the jet mixer can be the washing medium and the surrounding medium can be the crude nitrate ester to be purified; however, as an alternative, the (central) driving jet can also be formed by the crude nitrated product to be purified and the medium surrounding the (central) driving jet can be formed by the washing medium. Both alternative embodiments lead to the desired result. However, preference is given according to the invention to the (central) driving jet in the jet mixer being the washing medium and the surrounding medium being the crude nitrate ester to be purified.

Particularly good results in respect of the purification of the crude products to be purified are obtained when the dispersing or emulsifying device, in particular the mixing device, produces a driving jet (central jet) and an annular jet surrounding the driving jet (where the driving jet is preferably formed by the washing medium and the annular jet is preferably formed by the crude nitric esters to be purified), where the ratio of the velocities between the driving jet and the annular jet surrounding the driving jet is set in the range from 1:6 to 35:1, preferably in the range from 1:2 to 25:1, particularly preferably in the range from 1:1 to 12:1. In this way, particularly intimate and fine dispersion of firstly washing medium and secondly crude product to be purified and consequently particularly efficient purification are achieved.

The flow velocity of the emulsion or dispersion composed of washing medium and crude products in the tube reactor (i.e. downstream of the dispersing device) should be set in the range from 0.1 to 15.0 m/s, preferably from 0.5 to 10 m/s.

In an embodiment of the present invention, it can be provided for the dispersing or emulsifying device, in particular the mixing device, used in process step (a) to be installed upstream, in particular immediately upstream, of the tube reactor. In a particular variant of this embodiment, it can be provided for the dispersing or emulsifying device, in particular the mixing device, to go over into the tube reactor.

However, it is equally possible for the dispersing or emulsifying device, in particular the mixing device, to be integrated into the tube reactor or be a constituent of the tube reactor. For this purpose, the dispersing or emulsifying device can, for example, be arranged in the upper or upstream part of the tube reactor. Such an embodiment is, in particular, possible when the dispersing device, in particular the mixing device, is configured as jet mixer or as jet pump (injector).

As regards the residence time of the emulsion of firstly washing medium and secondly crude nitrate ester in the tube reactor (washing apparatus) during process step (b), this can vary within a wide range. Particular preference is given to the residence time in the tube reactor being from 0.05 to 130 seconds, preferably from 0.1 to 70 seconds, particularly preferably from 1 to 35 seconds. Particularly good washing results are achieved in this way, since firstly a sufficient minimum residence time and secondly also an economical throughput are ensured.

In the purification, the mass and phase ratios between crude nitrated products to be purified and washing medium are also of importance, and can vary within a wide range.

Particularly good results are obtained when the mass ratio between crude nitric esters to be purified and washing medium, in particular freshly added washing medium, is set in the range from 250:1 to 1:20, preferably in the range from 120:1 to 1:8, particularly preferably in the range from 12:1 to 1:3.

Likewise, particularly good results are obtained when the mass ratio between crude nitric esters to be purified and washing medium in the tube reactor and/or washing apparatus is set in the range from 30:1 to 1:6, preferably in the range from 15:1 to 1:5, particularly preferably in the range from 6:1 to 1:3.

Setting of the mass or phase ratio is achieved by circulation of the washing medium after phase separation. This ensures firstly an optimal exchange area between organic phase and washing medium and secondly a very short time for phase separation in the phase separation apparatus.

The washing of the crude nitrate esters can usually be carried out as a liquid/liquid wash in pure form, or else in admixture with an additional inert solvent. These additional solvents can either be separated off before further use or be used further directly as mixture of solvent/nitrate ester.

The washing medium used according to the invention is liquid under process conditions, in particular at temperatures above 5° C., preferably at temperatures above 25° C., and atmospheric pressure. Preference is given according to the invention to the washing medium being water-based, preferably being water.

Depending on the mass or phase ratio within the tube reactor (washing apparatus), the nitrate ester to be washed is dispersed in the washing medium as oil-in-water emulsion (O/W emulsion) or else the washing medium is dispersed in the nitrate ester to be washed as water-in-oil emulsion (W/O emulsion).

In a preferred embodiment, the process of the invention can be carried out continuously (although a discontinuous mode of operation is also possible in principle). When the process is carried out industrially, preference is in every case given to the process being carried out continuously.

The process of the invention can in principle be used for carrying out an acid wash and/or a basic wash and/or a neutral wash of the crude nitric esters to be purified.

In other words, the process of the invention is in principle suitable for carrying out the acid wash and/or the basic wash and/or the neutral wash of the crude nitrated products or the crude nitric esters. The process of the invention can thus be employed in all three abovementioned washing steps. However, it is likewise also possible for the process of the invention to be used for only one or two washing stages, for example only for the acid wash or only for the basic wash or only for the neutral wash. Thus, for example, the emulsion transport of nitrate esters between the individual process stages of a production plant and/or for further processing after washing which is typical of nitrate esters can be configured in accordance with the process of the invention. In this respect, the process of the invention can be used flexibly.

In a particular embodiment of the present invention, the process of the invention, in particular process steps (a) and (b), can be carried out repeatedly or be performed a number of times. In this case, the (partially) purified crude nitric esters which result after each pass through the process are again fed to the subsequent pass through the process.

In this particular embodiment, it can be provided for at least one pass through the process to be carried out as a basic wash and/or to be carried out using a basic washing medium and at least one subsequent pass through the process to be carried out as a neutral wash and/or carried out using a neutral washing medium.

As an alternative, it can also be provided for two, preferably three, sequential passes through the process to be carried out, optionally comprising a first wash with an acidic washing medium ("acid wash"), followed by a second wash with a basic washing medium ("basic wash") and again after this a third wash with a neutral washing medium ("neutral wash").

The efficiency of the washing medium can be increased further by at least one base, as described below, being added to the washing medium.

In other words, the invention can provide for at least one base to be added to the washing medium, in particular for carrying out a basic wash. This base can, in particular, be selected from the group consisting of inorganic hydroxides, carbonates, hydrogencarbonates and ammonia and also mixtures or combinations thereof.

The amount of alkali used in an alkaline wash should be sufficient for not only all acids to be able to be converted quantitatively into their salts but there should also be an excess of base so that the pH in the washing liquor is sufficiently high for even weak acids to be able to be quantitatively washed out. In this context, it is particularly advantageous for the content of base in the washing medium to be from 0.01 to 0.4 mol/l, preferably from 0.02 to 0.2 mol/l. In particular, the content of base in the washing medium should be at least twice the amount of alkali required for neutralization of all materials which are present as impurities and form salts with bases.

As indicated above, the crude nitric esters to be purified are liquid under process conditions. The crude nitric esters to be purified can optionally be present as a solution in an inert solvent, e.g. in halogen-containing hydrocarbons, in particular methylene chloride, dichloroethane, etc., or in other solvents which do not interfere in further processing or are used during further processing.

Process step (b) can then be followed by separation of the nitric esters which have been freed of impurities from the washing medium, preferably in a phase separation apparatus (separator).

As phase separation device or phase separation apparatus, it is possible to use all types of static separators, and also dynamic separators such as centrifugal separators. The separation time of the emulsion of nitrate ester/washing medium depends not only on the density difference between the two phases, the type of emulsion (W/O or O/W) and the mixing energy introduced but also on the excess of base in the washing medium which is not required for neutralization. When the same mixing energy is introduced, the separation time decreases significantly with increasing concentration of base in the washing medium. However, surface-active agents or mechanical separation aids, e.g. packings, separation plates, etc., can also be used for accelerating phase separation. The phase separation can also be accelerated by means of a spacing between the individual mixing elements which is matched to the nitrate ester and the type of emulsion.

In an advantageous embodiment of the process of the invention, the washing medium is, especially after separation of the nitrated nitric esters which have been freed of the impurities from the washing medium, recycled. In this way, efficient washing is made possible and the amount of washing medium is reduced to a minimum.

To remove impurities having high partition coefficients in favor of the nitrate ester to be washed, high mass transfer resistances in the organic phase and slow further reaction of the extracted impurities in the washing medium, e.g. nitrous gases or nitrogen dioxide, the residence time in the subsequent reactor should be matched to these circumstances. In a particular embodiment of the process of the invention, this can, for example, be achieved by means of a combination of the above-described devices for producing an optimal washing emulsion, e.g. by means of stirred vessels, in order to ensure the necessary residence time for phase transfer and the subsequent reaction.

The dispersion/emulsion present at the end of the mixing section can be separated again into the individual phases in a phase separation apparatus (separator or settler). The washing medium together with the impurities present therein can either be passed as wastewater to wastewater treatment or be introduced in countercurrent into the preceding washing stage.

The washed nitrate ester can either be fed to the next washing stage or at the end of washing be transferred directly to further processing or to an intermediate storage facility.

After washing or after the washing medium has been separated off (e.g. after separation of the washing emulsion in a static separator or by means of a centrifugal separator), traces of suspended and dissolved water may optionally be removed from the purified nitrate ester by means of additional drying, if desired.

As indicated above, the process of the invention is associated with many advantages and special features, of which some advantages and special features will be indicated below, but not conclusively and not in a restrictive manner.

In particular, the process of the invention allows efficient purification of crude nitrated products obtained in the nitration of nitratable monohydric and polyhydric (cyclo)aliphatic alcohols after removal of the residual nitrating acid with only a low degree of complexity and good process economics such as process efficiency.

The tube reactor employed according to the invention for purifying the crude nitration products makes it possible to produce large exchange areas for a two-phase mixture of washing medium and crude nitrate ester, so that effective mass transfer and rapid transfer of the impurities into the washing medium or, in the case of acidic compounds, rapid neutralization is ensured in this way.

The process of the invention allows rapid and at the same time efficient removal of the impurities originating from the nitration from the crude nitrated products, with the washing medium being able to be readily recycled or circulated after treatment of the nitrate esters.

Furthermore, the general safety when handling the highly sensitive multiply nitrated nitrate esters such as NGL or EGDN, etc., is improved further by the consistent use of the process of the invention. The amount of explosive substances present in the plant are reduced further.

The tube reactor with additional mixing elements which is used according to the invention not only allows efficient and intimate dispersion of washing medium and nitrated (cyclo) aliphatic alcohol in one another, but targeted setting of a defined dispersion of the nitrate ester to be washed in the washing medium over the entire length of the tube reactor reliably prevents, when the permissible tube cross sections are observed, partial coalescence of the dispersed nitrate ester in the tube reactor and thus prevents the formation of liquid threads of separated-out nitrate ester which could result in detonation.

The process of the invention is suitable for carrying out the acid wash and/or the basic wash and/or the neutral wash of the crude nitrated products. The process on the invention can thus be used in all three abovementioned washing steps. However, it is likewise possible to use the process of the invention for only one or two washing stages, for example only for the acid wash or only for the basic wash or only for the neutral wash. In this way, the emulsion transport of, for example, nitrate esters between the individual process stages of a production plant and/or to further processing after washing which is typical of nitrate esters can be configured according to the process of the invention. In this respect, the process of the invention can be used flexibly.

The present invention further provides, according to a second aspect of the present invention, an apparatus (plant) for removing impurities obtained in the preparation of aliphatic or cycloaliphatic nitric esters (nitrate esters), in particular for removing impurities from crude nitric esters obtained in the nitration of nitratable monohydric or polyhydric aliphatic or cycloaliphatic alcohols after removal of the residual nitrating acid, by treatment with at least one washing medium, where the apparatus of the invention is particularly suitable for carrying out a process as indicated above, wherein the apparatus comprises the following devices:

(a) at least one dispersing device, in particular at least one mixing device, for contacting and emulsifying crude nitric esters to be purified and washing medium; and, (b) arranged downstream of the dispersing device, a tube reactor for introduction of the emulsion of crude nitric esters to be purified and washing medium produced in the dispersing device, where the tube reactor is equipped with mixing elements, in particular for introduction of additional mixing energy, so that the impurities initially present in the crude nitric esters are at least partially removed during passage of the emulsion through the tube reactor and/or so that the impurities initially present in the crude nitric esters are at least partly transferred into the washing medium and/or neutralized thereby during passage of the emulsion through the tube reactor.

As indicated above in connection with the process of the invention, the dispersing device, in particular the mixing device, can be configured as jet mixer or pump, in particular jet pump (injector).

As has likewise been described above in the context of the process of the invention, the dispersing device, in particular the mixing device, can be configured in such a way that it produces a driving jet (central jet) and an annular jet surrounding the driving jet.

As has likewise been indicated in connection with the process of the invention, the dispersing device, in particular the mixing device, can be configured as jet mixer or jet pump (injector). Here, the jet mixer or the jet pump can, in particular, be configured so that a preferably central driving jet and a medium surrounding the driving jet, in particular in the form of an annular jet, can be produced.

As stated above in connection with the process of the invention, the dispersing device, in particular the mixing device, can be installed upstream, in particular directly upstream, of the reactor, with, in a particular embodiment, the dispersing device, in particular the mixing device, being able to go over into the tube reactor.

In an alternative embodiment, the dispersing device, in particular the mixing device, can be integrated into the tube reactor and/or be a constituent of the tube reactor. In this respect, reference may be made to what has been said above in connection with the process of the invention.

As explained above in the description of the process of the invention, the tube reactor is equipped with mixing elements, in particular for introducing additional mixing energy. As regards further details, reference may be made to the process of the invention.

A one-, two- or three-stage wash of the crude nitration product (i.e. acid wash and/or basic wash and/or neutral wash) can be carried out in the apparatus of the invention.

Furthermore, it can be provided, according to the invention, for a separation device, in particular a separator, for separating the nitrated products which have been freed of the impurities from the washing medium to be arranged downstream of the tube reactor.

Furthermore, it is possible in the apparatus of the invention for a stirred vessel and or a stirred reactor to be arranged downstream of the tube reactor and upstream of the separation device (i.e., in other words, between tube reactor and separation device). In particular, the contact and/or residence time between nitrated products (nitric esters) and the washing medium is prolonged in this way.

For further details regarding the apparatus or plant of the invention, reference may be made, in order to avoid unnecessary repetition, to what has been said above in respect of the process of the invention, which applies analogously to the apparatus or plant of the invention.

Finally, the present invention further provides, according to a third aspect of the present invention, a production plant for the preparation of nitric esters of monohydric or polyhydric aliphatic or cycloaliphatic alcohols and/or for the nitration of monohydric or polyhydric aliphatic or cycloaliphatic alcohols with subsequent purification of the crude nitrated products formed in the nitration, wherein the production plant comprises the following units:
(a) a nitration unit for the preparation of nitric esters of monohydric or polyhydric aliphatic or cycloaliphatic alcohols and/or for the nitration of monohydric or polyhydric aliphatic or cycloaliphatic alcohols, in particular with one or more appropriate reaction vessels for carrying out the nitration reaction(s);
(b) optionally, arranged downstream of the nitration unit in the production line, a separation device, in particular a separator, in particular for the removal of the residual nitrating acid from the nitrated crude products (crude nitric esters);
(c) arranged downstream of the nitration unit and any separation device present in the production line, a washing facility for carrying out washing of the crude nitrated products, where the washing facility comprises:
at least one dispersing device, in particular at least one mixing device, for contacting and emulsifying crude nitric esters to be purified and washing medium; and, arranged downstream of the dispersing device, a tube reactor for introduction of the emulsion of crude nitric esters to be purified and washing medium which has been produced in the dispersing device, where the tube reactor is equipped with mixing elements, in particular for introducing additional mixing energy, so that the impurities initially present in the crude nitric esters are at least partially removed during passage of the emulsion through the tube reactor and/or so that the impurities initially present in the crude nitric esters are at least partly transferred into the washing medium and/or neutralized thereby during passage of the emulsion through the tube reactor;
(d) optionally, arranged downstream of the washing facility in the production line, a stirred vessel, in particular for increasing the contact and/or residence time between nitric esters and washing medium;
(e) arranged downstream of the washing unit and any stirred vessel present in the production line, a separation device, in particular a separator, in particular for separating the nitric esters which have been freed of the impurities from the washing medium.

In other words, the above-described apparatus or plant for purification, i.e. for the removal of impurities, is a constituent, namely in the form of the washing unit or washing facility (c), of the production plant of the invention.

As indicated above, the mixing elements in the tube reactor can be static mixing elements or be configured as static mixing elements.

In a particular embodiment, the mixing elements, in particular the static mixing elements, can be fixed to the inside in the tube reactor, in particular be joined permanently or releasably to the interior walls of the tube reactor.

As an alternative, the mixing elements can also be configured as push-in elements. Here, the push-in elements can be inserted as required according to number and/or position into the tube reactor or positioned in the tube reactor.

As indicated above, the mixing elements can be configured as metal plates, in particular impingement or deflection plates, as orifice plates, as static mixers or as flow dividers.

In particular, from 1 to 15 mixing elements, in particular from 2 to 15 mixing elements, preferably from 2 to 10 mixing elements, particularly preferably from 2 to 5 mixing elements, can be arranged in the tube reactor. As indicated above, it is advantageous for a mixing energy (i.e. volume-based mixing energy) of from 20 to 1000 joule/liter, preferably from 25 to 500 joule/liter, particularly preferably from 30 to 200 joule/liter, to be introduced by the mixing elements in the tube reactor and/or for the pressure drop per mixing element to be from 0.2 bar to 3.0 bar, preferably from 0.3 to 1.5 bar, particularly preferably from 0.3 to 0.8 bar.

As indicated above in connection with the process of the invention and the apparatus or plant of the invention, the dispersing device, in particular the mixing device, can be configured as jet mixer or pump, in particular jet pump (injector).

Furthermore, the dispersing device, in particular the mixing device, can be configured so that it produces a driving jet (central jet) and an annular jet surrounding the driving jet.

In a particular embodiment, the dispersing device, in particular the mixing device, can be configured as jet mixer or jet pump (injector). Here, the jet mixer or the jet pump can be configured so that a preferably central driving jet and a medium surrounding the driving jet, in particular in the form of an annular jet, can be produced.

As indicated above, the dispersing device, in particular the mixing device, can be upstream, in particular directly upstream, of the reactor. In this embodiment, the dispersing device, in particular the mixing device, can go over into the tube reactor.

In an alternative embodiment, the dispersing device, in particular the mixing device, can also be integrated into the tube reactor or be a constituent of the tube reactor.

For further details regarding the production plant of the invention, reference may be made to what has been said above in respect of the process of the invention and the apparatus or plant of the invention, which applies analogously to the production plant of the invention.

The process of the invention and the apparatus or plant of the invention for purification and also the production plant of the invention for nitration are illustrated by way of example and in a nonrestrictive way in the attached figures.

Figure 1:
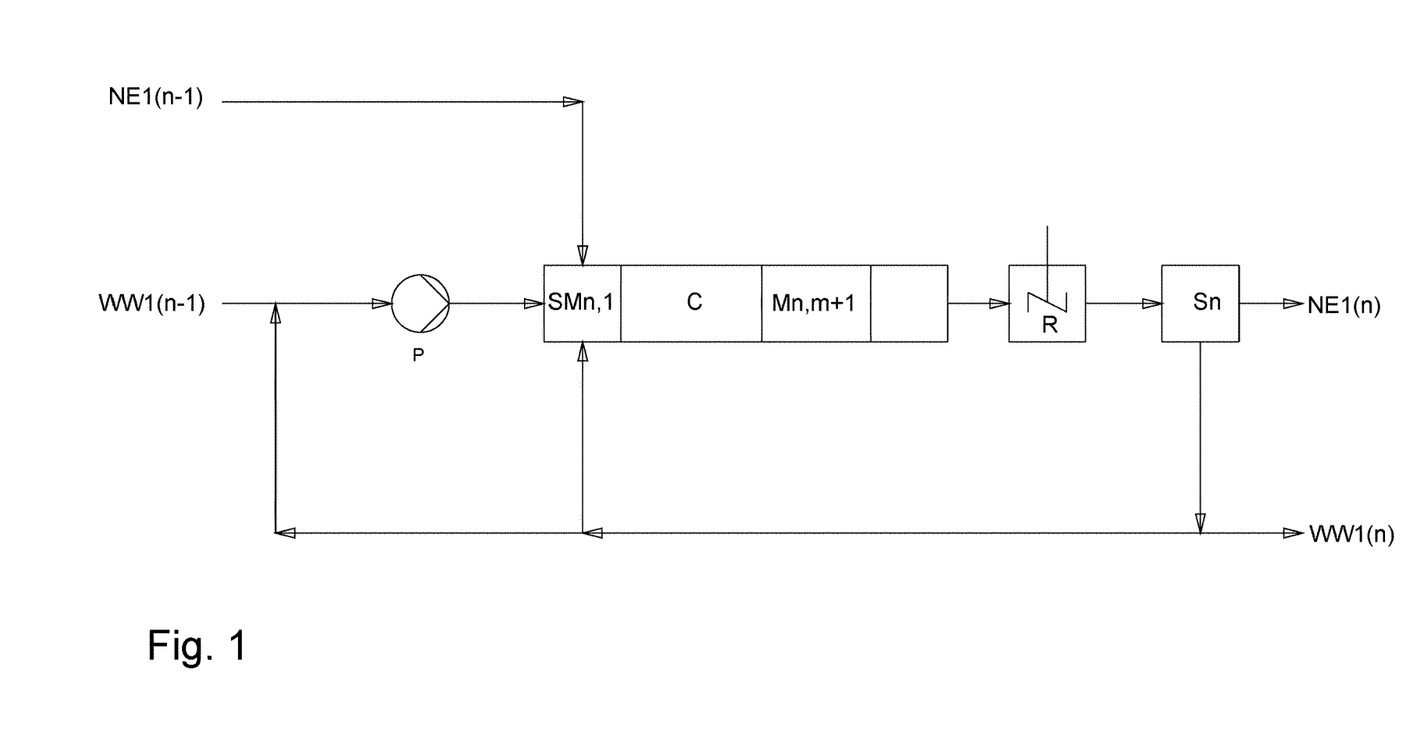
FIG. 1 provides a schematic depiction of a single-stage wash for crude nitrate esters according to the process of the invention or using the apparatus of the invention.
Figure 3:
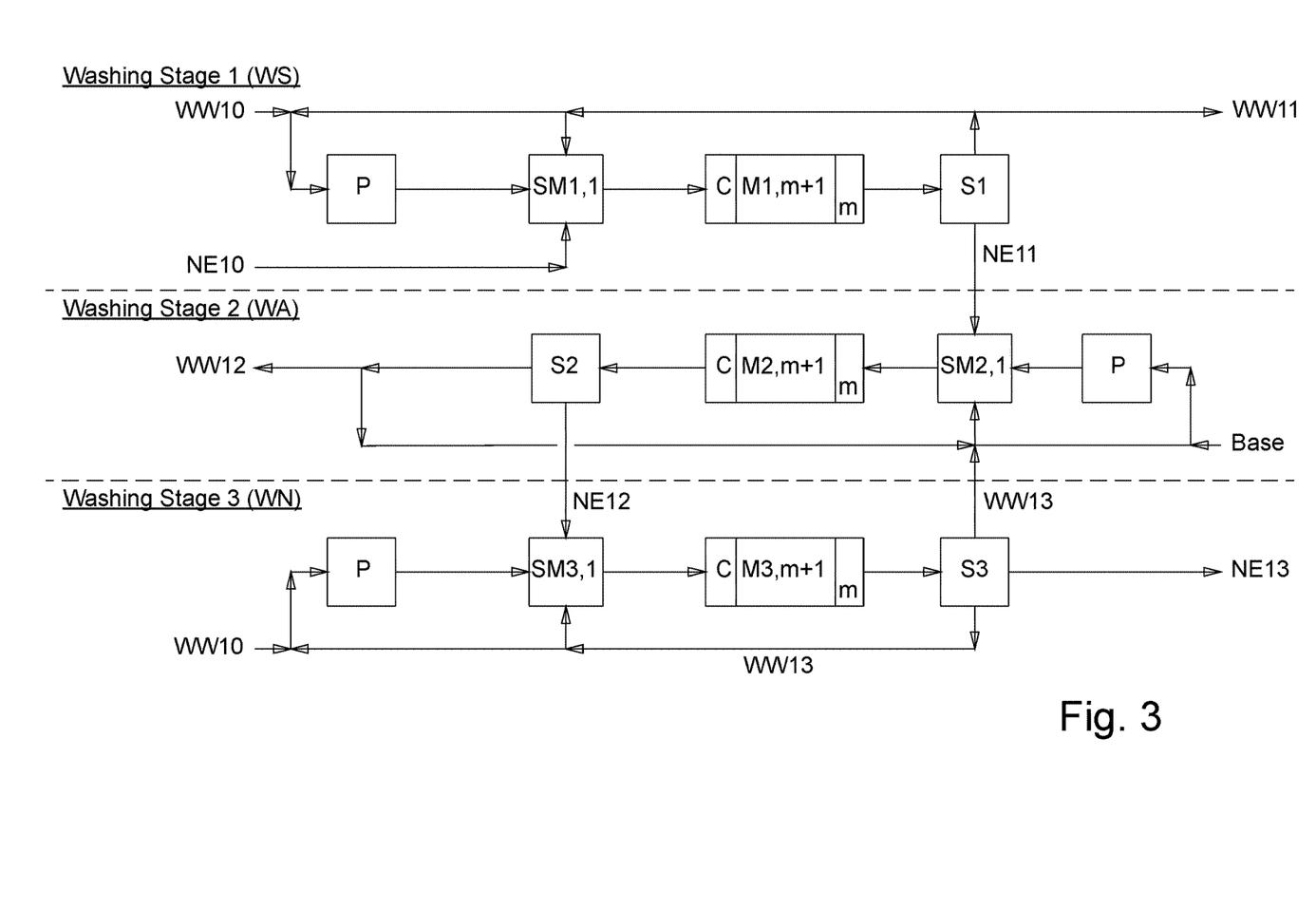
FIG. 3 provides a schematic depiction of a process flow of the process of the invention or a schematic depiction of the apparatus or plant of the invention as per a preferred working example of the invention for the usual three washing stages for washing nitrate esters.
Figure 4:
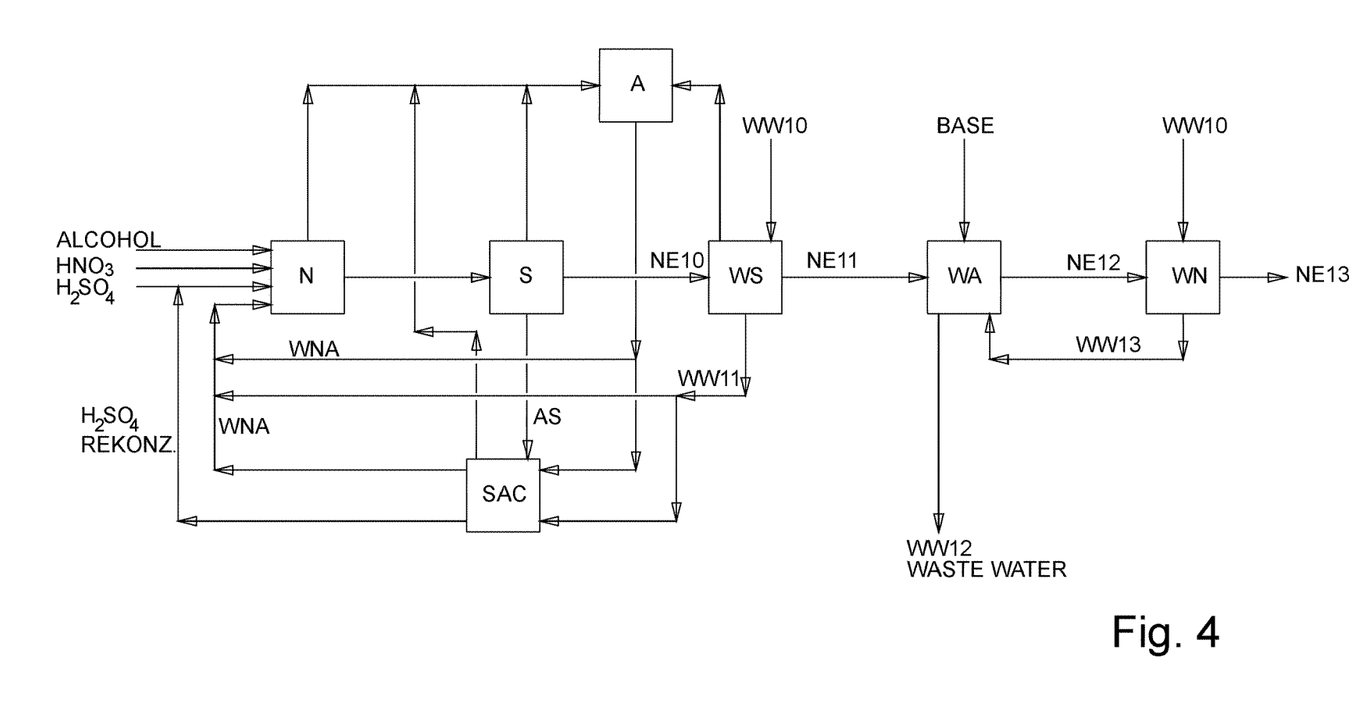
FIG. 4 provides a schematic depiction of a production plant according to the invention for the nitration of nitratable monohydric and polyhydric alcohols with subsequent washing of the resulting nitrate esters as per a preferred working example of the invention.

Further advantages, properties, aspects and features of the present invention may be derived from the following description of embodiments which are preferred according to the invention and are depicted in the drawings. The drawings show:

FIG. 1 a schematic depiction of a single-stage wash for crude nitrate esters according to the process of the invention or using the apparatus of the invention;

FIG. 2 a detailed depiction of individual parts of the apparatus as per the schematic depiction of the process of the invention in FIG. 1;

FIG. 3 a schematic depiction of a process flow of the process of the invention or a schematic depiction of the apparatus or plant of the invention as per a preferred working example of the invention for the usual three washing stages for washing nitrate esters;

FIG. 4 a schematic depiction of a production plant according to the invention for the nitration of nitratable monohydric and polyhydric alcohols with subsequent washing of the resulting nitrate esters as per a preferred working example of the invention.

FIG. 1 shows, in a schematic depiction, an embodiment of a washing stage according to the process of the invention or using the apparatus or plant of the invention for washing crude nitrate esters with the washing medium as driving jet.

The crude nitrate ester NE1($n$−1) where n=1-3 to be washed is, after removal of the residual nitrating acid, introduced into a wash WW1($n$−1) where n=1-3, i.e. into an acid wash WS where n=1 or, after removal of all other weakly acidic materials from the oxidative degradation of impurities in the presence of bases which are still dissolved in the nitrate ester, into an alkaline wash WA where n=2 or into a neutral wash WN where n=3, combined with the washing medium WW10 (fresh water) or WW1$n$ where n=1-3, which in the case depicted serves as driving jet, in a mixing device SMn,1 where n=1-3, preferably in a jet pump (injector) or a jet mixer, and introduced directly into a tube reactor C which contains the additional mixing elements Mn,m+1 where n=1-3 and where m=1-15.

The washing emulsion from the tube reactor is, either directly or, if necessary, after a prolonged residence time in a residence vessel (e.g. in a stirred vessel R, etc.), separated into the phases in a separation apparatus Sn where n=1-3.

The washed nitrate ester NE1$n$ where n=1-3 is either fed to the subsequent washing stage or passed as fully washed product NE13 to further processing. The loaded washing medium WW1$n$ where n=1-3 is either directly discharged as wastewater or else recirculated as substream for setting a defined phase ratio between nitrate ester and washing medium. This recirculated substream can be directly fed, either together with the freshly added washing water as driving jet or as circulating stream, into the tube reactor.

Figure 2A:
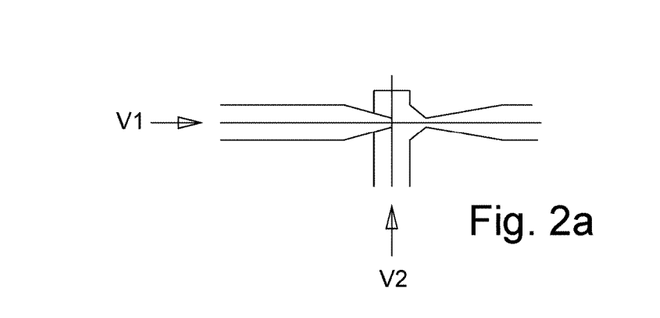
FIG. 2 provides a detailed depiction of individual parts of the apparatus as per the schematic depiction of the process of the invention in FIG. 1.
Figure 2B:
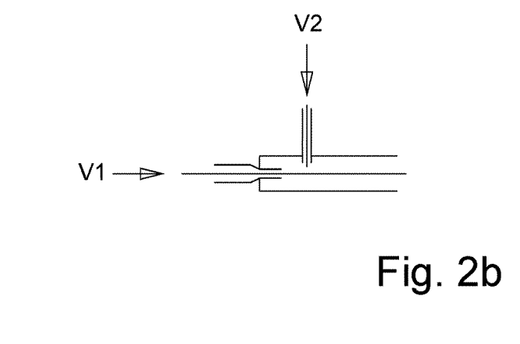
Figure 2C:
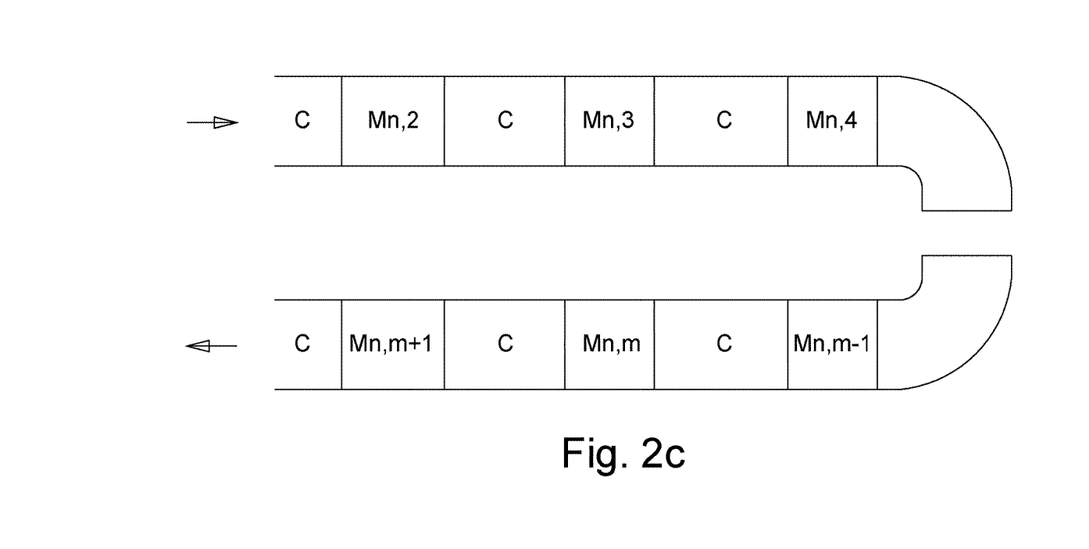

The depictions of FIGS. 2a-2c show the mixing devices SMn,1 where n=1-3 schematically depicted in FIG. 1, as jet pump (FIG. 2a) and as jet mixer (FIG. 2b), where V1 denotes the driving jet (preferably washing medium) and V2 denotes the nitrate ester. A possible arrangement of the static mixing elements Mn,2, Mn,3, Mn,4, Mn,m−1, Mn,m and Mn,m+1 in the tube reactor, distributed over the total length of the tube reactor, is additionally depicted in FIG. 2c.

FIG. 3 shows an example of the process of the invention in three steps for the separate removal of the mineral acids by means of an acid wash (WS), for the removal of all weakly acidic materials from the oxidative degradation of impurities which are still present in the presence of bases in the alkaline range by means of an alkaline wash (WA) and for the removal of traces of entrained alkaline washing liquor by means of a neutral wash (WN):

a) In step 1, the sulfuric and nitric acid suspended and dissolved in the crude nitrate ester NE 10 is removed by washing with fresh water WW 10 in a single-stage acid wash WS. The washing water WW 10 and recirculated washing water WW 11 as driving jet are fed directly by means of pump P together with the nitrate ester NE 10 to be washed using a jet pump (injector) or via a jet mixer into a tube reactor which contains additional mixing elements M1,$m$+1. After passage through the tube reactor, the emulsion formed is separated in a separator S1. After phase separation, the washing medium is either discharged directly as wastewater WW 11 or, as an alternative, a substream is additionally circulated in order to set a prescribed phase ratio and thus a defined type of emulsion. The nitrate ester NA 11 which has been freed of mineral acids is fed into washing stage 2, viz. the alkaline wash WA.

b) In step 2, all remaining dissolved mineral acids and other acidic materials from the oxidative degradation of impurities are removed in a single-stage alkaline wash WA. The washing water WW 13 from the neutral wash and recirculated washing water WW12 as driving jet are fed directly with addition of a base by means of pump P together with the nitrate ester NE 11 to be washed from the acidic wash WS using a jet pump (injector) or via a jet mixer into a tube reactor which contains additional mixing elements M2,$m$+1. After passage through the tube reactor, the emulsion formed is separated in a separator S2. The wastewater WW 12 having a pH of greater than 7.5 is either discharged directly or, as an alternative, a part thereof can be circulated in order to set a prescribed phase ratio and thus a defined type of emulsion. The nitrate ester NA 12 which has been freed of all mineral acids and other acidic materials from the oxidative degradation of impurities is fed into the washing stage 3, viz. the neutral wash WN.

c) In step 3, the entrained traces of washing medium from the alkaline wash are removed in a single-stage neutral wash WN. The washing water WW 10 and recirculated washing water WW 13 as driving jet are fed directly by means of pump P together with the nitrate ester NE 12 to be washed using a jet pump (injector) or via a jet mixer into a tube reactor which contains additional mixing elements M3,$n$+1. After passage through the tube reactor, the emulsion formed is separated in a separator S3. The washing medium which contains the residual traces of alkali and impurities is either introduced directly as wastewater WW 13 into the second washing stage WA or, as an alternative, a part thereof can be additionally circulated in order to set a prescribed phase ratio and thus a defined type of emulsion. The nitrate ester NE 13 which has been freed of mineral acids and other acidic materials from the oxidative degradation of impurities and residual traces of alkali is passed directly to further processing or, after removal of any inert solvents present, to an intermediate storage facility.

FIG. 4 shows an example of a production plant according to the invention for the preparation of nitrate esters with integrated washing according to the invention of the crude nitrate esters from an isothermal or adiabatic nitration. The crude nitrate ester NE 10 formed in the nitration unit N by reaction of the alcohol to be nitrated with nitric acid in the presence of sulfuric acid is, after removal of the nitrating acid in the separator S, washed in the acid wash WS using water WW 10 in the manner according to the invention. After phase separation, the resulting wastewater WW 11 which contains all washed-out sulfuric and nitric acid is fed together with the nitric acid WNA obtained from the offgas treatment of the nitration plant in an absorber plant A either directly or after concentration in an SAC plant SAC together with the residual acid AS from the nitration back into the nitration or is discharged as wastewater to be treated.

The nitrate ester NE 11 which has been freed of the mineral acids is washed in one stage in the washing stage 2 (i.e. alkaline wash WA) in the presence of bases according to the process of the invention. After phase separation, the wastewater WW12 which originates from the alkaline wash and has a pH in the range from 7.5 to 13 and still contains all other acidic materials from the oxidative degradation of impurities is fed to additional treatment before discharge into a main outfall drain. The nitrate ester NA 12 from the alkaline wash WA is fed into the neutral wash WN and washed in one stage with water WW 10 according to the process of the invention. After phase separation, the wastewater WW 13 coming from the neutral wash WN is fed together with base into the alkaline washing stage 2 (WA). The washed nitrate ester NA 13 is passed directly to further processing or introduced into an intermediate storage facility.

Further embodiments, modifications, variations of the present invention will be able to be readily recognized and realized by a person skilled in the art on reading the description, without going outside the scope of the present invention.

The present invention is illustrated by the following working examples, but without the present invention being restricted thereto.

WORKING EXAMPLES

Washing of Ethylhexyl Nitrate (EHN)

In the following working examples, the washing of a crude, i.e. still unwashed and contaminated with by-products originating from the nitration and unreacted starting chemicals, ethylhexyl nitrate coming from the nitration is described. The objective is, inter alia, to obtain a total acid content of less than 30 ppm, calculated as nitric acid (normal commercial product specification).

Even though the process of the invention or the apparatus of the invention is illustrated using ethylhexyl nitrate (EHN) as nitrate ester to be purified in the following working examples, the process and the apparatus of the present invention are not restricted thereto but are applicable to any other nitrate esters, e.g. nitrate esters from the nitration of glycerol, trimethylolpropane, propanediol, ethylene glycol, diethylene glycol and triethylene glycol, etc., and can be carried out using any other bases instead of sodium hydroxide for the alkaline wash.

Example 1: Three-Stage Washing of EHN (According to the Invention)

Example 1.1: Single-Stage Acid Wash

Unwashed ethylhexyl nitrate (EHN) (134.7 g/min) from a continuous nitration of ethylhexanol as per EP 1 792 891 A1 having a residual content of sulfuric acid (0.13%), nitric acid (0.84%) and ethylhexanol (about 0.4%) was fed together with 67 g/min of demineralized water and circulated washing acid in a ratio of 1:1 by means of a jet mixer (injector) using the washing medium as central jet at room temperature (about 21° C.) into a tube reactor which additionally contained three static mixing elements. The relative velocity between central jets and EHN to be washed was about 8:1. The residence time in the tube reactor was not more than 5 seconds. The pressure drop over the total length of the tube reactor was about 0.9 bar (corresponding to a mixing energy of about 90 joule/l). After phase separation, the EHN still contained about 2700 ppm of acid (reported as nitric acid); the washing water contained about 0.25% of sulfuric acid and about 1.65% of nitric acid.

Example 1.2: Single-Stage Alkaline Wash

The ethylhexyl nitrate (EHN) originating from the acid wash as per example 1.1 (133.3 g/min) having a residual content of acid of about 2700 ppm (reported as nitric acid) was fed together with 67 g/min of an aqueous solution containing ammonia (0.16%, i.e. 10% excess) and circulated washing liquor in a ratio of 1:1 by means of a jet mixer (injector) using the washing medium as central jet at room temperature (about 21° C.) into a tube reactor which additionally contained three static mixing elements. The relative velocity between central jet and EHN to be washed was about 8:1. The residence time in the tube reactor was not more than 5 seconds. The pressure drop over the total length of the tube reactor was about 0.9 bar (corresponding to a mixing energy of about 90 joule/l). After phase separation, the EHN still contained about 29 ppm of acid (reported as nitric acid).

Example 1.3: Single-Stage Neutral Wash

The ethylhexyl nitrate (EHN) (133 g/min) originating from the alkaline wash as per example 1.2 having a residual content of acid of about 29 ppm (reported as nitric acid) was fed together with 67 g/of demineralized water and circulated washing water in a ratio of 1:1 by means of a jet mixer (injector) using the washing medium as central jet at room temperature (about 21° C.) into a tube reactor which additionally contained three static mixing elements. The relative velocity between central jet and EHN to be washed was about 8:1. The residence time in the tube reactor was not more than 5 seconds. The pressure drop over the total length of the tube reactor was about 0.9 bar (corresponding to a mixing energy of about 90 joule/l). After phase separation, the EHN still contained about 0.1 ppm of acid (reported as nitric acid).

Example 2: Washing of EHN (Comparison)

Example 2.1: Single-Stage Alkaline Wash

Ethylhexyl nitrate (EHN) (133.3 g/min) from an acid wash, as described in example 1.1, having a residual content of acid of about 2700 ppm (reported as nitric acid) was fed together with 67 g/min of an aqueous solution containing ammonia (0.16%, i.e. 10% excess) and circulated washing liquor in a ratio of 1:1 by means of a jet mixer (injector) using the washing medium as central jet at room temperature (about 21° C.) into a tube reactor which, however, did not contain any static mixing elements. The relative velocity between central jet and EHN to be washed was about 8:1. The residence time in the tube reactor was not more than 5 seconds. The pressure drop over the total length of the tube reactor was about 0.10 bar (corresponding to a mixing energy of about 10 joule/l). After phase separation, the EHN still contained about 1200 ppm of acid (reported as nitric acid).

Example 2.2: Single-Stage Neutral Wash

The ethylhexyl nitrate (EHN) (133.3 g/min) originating from the alkaline wash as per example 2.1 having a residual content of acid of about 1200 ppm (reported as nitric acid) was fed together with 67 g/min of demineralized water and circulated washing water in a ratio of 1:1 by means of a jet mixer (injector) using the washing medium as central jet at room temperature (about 21° C.) into a tube reactor which did not contain any static mixing elements. The relative velocity between central jet and EHN to be washed was about 8:1. The residence time in the tube reactor was not more than 5 seconds. The pressure drop over the total length of the tube reactor was about 0.10 bar (corresponding to a mixing energy of about 10 joule/l). After phase separation, the EHN still contained about 456 ppm of acid (reported as nitric acid).

Example 3: Single-Stage Wash of EHN (According to the Invention)

Unwashed ethylhexyl nitrate (EHN) (134.7 g/min) from a continuous nitration of ethylhexanol as per EP 1 792 891 A1 having a residual content of sulfuric acid (0.13%), nitric acid (0.84%) and ethylhexanol (about 0.4%) was fed together with 67 g/min of an aqueous solution containing ammonia (0.6%) and circulated washing liquor in a ratio of 1:1 by means of a jet mixer (injector) using the washing medium as central jet at room temperature (about 21° C.) into a tube reactor which additionally contained six static mixing elements. The relative velocity between central jet and EHN to be washed was about 8:1. The residence time in the tube reactor was not more than 5 seconds. The pressure drop over the total length of the tube reactor was about 1.8 bar (corresponding to a mixing energy of about 180 joule/l). After phase separation, the EHN still contained about 26 ppm of acid (reported as nitric acid).

The invention claimed is:

1. A process for removing impurities obtained in the preparation of aliphatic or cycloaliphatic nitric esters,
wherein the process comprises removing impurities from crude nitric esters obtained in the nitration of nitratable monohydric or polyhydric aliphatic or cycloaliphatic alcohols, after removal of the residual nitrating acid, by treatment with at least one washing medium,
wherein the process comprises the following process steps:
(a) the crude nitric esters are firstly brought into contact with a washing medium, wherein the crude nitric esters and the washing medium are dispersed in one another in such a way that an emulsion results; and then
(b) the resulting emulsion is subsequently fed into a tube reactor, which is equipped with mixing elements for introducing additional mixing energy, so that the impurities initially present in the crude nitric esters are at least partly removed during passage of the emulsion through the tube reactor, wherein the impurities initially present in the crude nitric esters are at least partly transferred into the washing medium and are neutralized thereby during passage of the emulsion through the tube reactor.

2. The process as claimed in claim 1,
wherein the nitric esters to be purified are selected from the group consisting of:
(i) nitric esters of aliphatic or cycloaliphatic monoalcohols;
(ii) nitric esters of dihydric aliphatic alcohols;
(iii) nitric esters of trihydric aliphatic alcohols; and
(iv) nitric esters of tetrahydric or polyhydric aliphatic alcohols.

3. The process as claimed in claim 1, wherein the mixing elements are configured as static mixing elements.

4. The process as claimed in claim 1,
wherein the mixing elements are fixed to the inside of the tube reactor; or
wherein the mixing elements are configured as push-in elements, with the push-in elements being inserted as required according to number and position in the tube reactor.

5. The process as claimed in claim 1, wherein the mixing elements are configured as metal plates, as impingement plates, as deflection plates, as orifice plates, as static mixers or as flow dividers.

6. The process as claimed in claim 1, wherein a volume-based mixing energy of from 20 to 1000 joule/liter is introduced by the mixing elements.

7. The process as claimed in claim 1, wherein the pressure drop per mixing element is from 0.2 bar to 3.0 bar.

8. The process as claimed in claim 1, wherein the production of the emulsion in step (a) is carried out by means of a dispersing device, with a jet mixer or pump being used as dispersing device.

9. The process as claimed in claim 1, wherein the production of the emulsion in step (a) is carried out by means of a dispersing device, with the mixing device producing a central driving jet and an annular jet surrounding the driving jet, wherein the central driving jet is formed by the washing medium and the annular jet is formed by the crude nitric esters to be purified.

10. The process as claimed in claim 1, wherein the production of the emulsion in step (a) is carried out by means of a dispersing device, with the mixing device producing a central driving jet and an annular jet surrounding the driving jet, wherein the ratio of the velocities between the central driving jet and the annular jet surrounding the driving jet is set in the range of from 1:6 to 35:1.

11. The process as claimed in claim 1,
wherein the residence time of the crude nitric esters to be purified in the tube reactor is from 0.05 to 130 seconds; and
wherein the mass ratio between crude nitric esters to be purified and washing medium is set in the range from 250:1 to 1:20.

12. The process as claimed in claim 1, wherein at least one base is added to the washing medium, with the base being selected from the group consisting of inorganic hydroxides, carbonates, hydrogencarbonates and ammonia and mixtures or combinations thereof.

13. The process as claimed in claim 1,
wherein the process steps (a) and (b) are carried out repeatedly, with the purified crude nitric esters resulting after a pass through the process in each case being fed again into the subsequent pass through the process;
wherein process step (b) is followed by a separation of the nitric esters, which have been freed of the impurities from the washing medium, in a phase separation device; and wherein the washing medium is recycled after separation of the nitric esters which have been freed of the impurities from the washing medium.

14. A process for removing impurities obtained in the preparation of aliphatic or cycloaliphatic nitric esters,
wherein the process comprises removing impurities from crude nitric esters obtained in the nitration of nitratable monohydric or polyhydric aliphatic or cycloaliphatic alcohols, after removal of the residual nitrating acid, by treatment with at least one washing medium,
wherein the process comprises the following process steps:
(a) the crude nitric esters are firstly brought into contact with a washing medium, wherein the crude nitric esters and the washing medium are dispersed in one another in such a way that an emulsion results; and then
(b) the resulting emulsion is subsequently fed into a tube reactor, which is equipped with mixing elements for introducing additional mixing energy, so that the impurities initially present in the crude nitric esters are at least partly removed during passage of the emulsion through the tube reactor, wherein the impurities initially present in the crude nitric esters are at least partly transferred into the washing medium and are neutralized thereby during passage of the emulsion through the tube reactor;
wherein the nitric esters to be purified are selected from the group consisting of:
(i) nitric esters of aliphatic or cycloaliphatic monoalcohols;
(ii) nitric esters of dihydric aliphatic alcohols;
(iii) nitric esters of trihydric aliphatic alcohols; and
(iv) nitric esters of tetrahydric or polyhydric aliphatic alcohols.

15. A process for removing impurities obtained in the preparation of aliphatic or cycloaliphatic nitric esters,
wherein the process comprises removing impurities from crude nitric esters obtained in the nitration of nitratable monohydric or polyhydric aliphatic or cycloaliphatic alcohols, after removal of the residual nitrating acid, by treatment with at least one washing medium,
wherein the process comprises the following process steps:
(a) the crude nitric esters are firstly brought into contact with a washing medium, wherein the crude nitric esters and the washing medium are dispersed in one another in such a way that an emulsion results; and then
(b) the resulting emulsion is subsequently fed into a tube reactor, which is equipped with mixing elements for introducing additional mixing energy, so that the impurities initially present in the crude nitric esters are at least partly removed during passage of the emulsion through the tube reactor, wherein the impurities initially present in the crude nitric esters are at least partly transferred into the washing medium and are neutralized thereby during passage of the emulsion through the tube reactor;
wherein the nitric esters to be purified are selected from the group consisting of:
(i) nitric esters of aliphatic or cycloaliphatic monoalcohols;
(ii) nitric esters of dihydric aliphatic alcohols;
(iii) nitric esters of trihydric aliphatic alcohols; and
(iv) nitric esters of tetrahydric or polyhydric aliphatic alcohols; and
wherein the mixing elements are configured as static mixing elements.

16. A process for removing impurities obtained in the preparation of aliphatic or cycloaliphatic nitric esters,
wherein the process comprises removing impurities from crude nitric esters obtained in the nitration of nitratable monohydric or polyhydric aliphatic or cycloaliphatic alcohols, after removal of the residual nitrating acid, by treatment with at least one washing medium,
wherein the process comprises the following process steps:
(a) the crude nitric esters are firstly brought into contact with a washing medium, wherein the crude nitric esters and the washing medium are dispersed in one another in such a way that an emulsion results; and then
(b) the resulting emulsion is subsequently fed into a tube reactor, which is equipped with mixing elements for introducing additional mixing energy, so that the impurities initially present in the crude nitric esters are at least partly removed during passage of the emulsion through the tube reactor, wherein the impurities initially present in the crude nitric esters are at least partly transferred into the washing medium and are neutralized thereby during passage of the emulsion through the tube reactor;
wherein the nitric esters to be purified are selected from the group consisting of:
(i) nitric esters of aliphatic or cycloaliphatic monoalcohols;
(ii) nitric esters of dihydric aliphatic alcohols;
(iii) nitric esters of trihydric aliphatic alcohols; and
(iv) nitric esters of tetrahydric or polyhydric aliphatic alcohols; and
wherein the mixing elements are configured as static mixing elements,
wherein the pressure drop per mixing element is from 0.2 bar to 3.0 bar, and
wherein a volume-based mixing energy of from 20 to 1000 joule/liter is introduced by the mixing elements.

* * * * *